United States Patent [19]

Kneafsey et al.

[11] Patent Number: 4,912,183
[45] Date of Patent: Mar. 27, 1990

[54] POLYMERIZATION CATALYSTS AND POLYMERIZATION PROCESS USING SUCH CATALYSTS

[75] Inventors: Brendan Kneafsey, Dublin, Ireland; John M. Rooney, South Glastonbury, Conn.; Stephen J. Harris, Dublin, Ireland

[73] Assignee: Loctite (Ireland) Ltd., Tallaght, Ireland

[21] Appl. No.: 178,103

[22] Filed: Apr. 6, 1988

Related U.S. Application Data

[63] Continuation-in-part of Ser. No. 88,945, Aug. 24, 1987, Pat. No. 4,866,198, which is a continuation-in-part of Ser. No. 870,677, Jun. 19, 1986, Pat. No. 4,699,966, which is a continuation-in-part of Ser. No. 717,251, Mar. 28, 1985, Pat. No. 4,642,362, which is a continuation-in-part of Ser. No. 825,012, Jan. 31, 1986, Pat. No. 4,695,615, which is a continuation-in-part of Ser. No. 914,491, Oct. 2, 1986, Pat. No. 4,718,966.

[51] Int. Cl.$^4$ .............................. C08F 4/44; C08F 2/00
[52] U.S. Cl. ..................................... 526/202; 526/207; 526/208; 526/245; 526/264; 526/301; 526/319
[58] Field of Search ............... 526/209, 202, 208, 207, 526/264, 245, 301, 319

[56] References Cited

U.S. PATENT DOCUMENTS

| | | | |
|---|---|---|---|
| 3,672,942 | 6/1972 | Neumann et al. | 427/295 |
| 4,054,480 | 10/1977 | Skoultchi et al. | 526/320 |
| 4,326,049 | 4/1982 | Rasmussen | 526/328 |
| 4,556,700 | 12/1985 | Harris et al. | |
| 4,617,336 | 10/1986 | Pastor et al. | |
| 4,622,414 | 11/1986 | McKervey | |
| 4,636,539 | 1/1987 | Harris et al. | 526/209 |
| 4,642,362 | 2/1987 | Harris et al. | 556/419 |
| 4,695,615 | 9/1987 | Leonard et al. | |
| 4,699,966 | 10/1987 | Harris et al. | |
| 4,718,966 | 1/1988 | Harris et al. | 526/209 |

FOREIGN PATENT DOCUMENTS 0196895 10/1986 European Pat. Off. .
025016 3/1988 European Pat. Off. .

Primary Examiner—Joseph L. Schofer
Assistant Examiner—N. Sarofin
Attorney, Agent, or Firm—Edward K. Welch, II; Eugene F. Miller

[57] ABSTRACT

A free radical polymerization process comprises bringing together
(a) a monomeric material such as an acrylic monomer in a relatively low polarity medium
(b) a free radical source or initiator such as a metallic salt initiator or activator normally soluble only in high polarity media such as water and
(c) a calixarene derivative of the formula I:

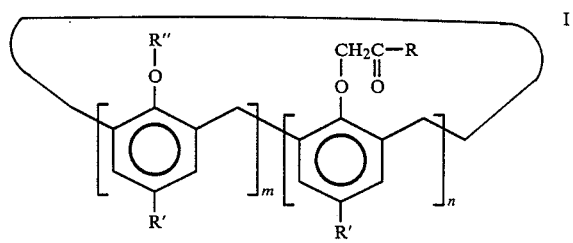

wherein m+n=4, 6 or 8
n=an integer greater than or equal to ½ (m+n)
wherein m+n=4,6 or 8
n=an integer greater than or equal to ½ (m+n)
R=hydrocarbyl, hydrocarbyloxy, substituted hydrocarbyl, substituted hydrocarbyloxy, aryl, hydrocarbylaryl, aryloxy, hydrocarbylaryloxy, substituted aryl, substituted hydrocarbylaryl, substituted aryloxy, or substituted hydrocarbylaryloxy;
R'=H, hydrocarbyl, aryl, hydrocarbylaryl, substituted hydrocarbyl, substituted aryl, or substituted hydrocarbylaryl;
R''=H, hydrocarbyl or substituted hydrocarbyl.

A free radical polymerization catalyst comprises a combination of a water-soluble, organic-insoluble initiator and a calixarene derivative of formula I.

A gap-filling adhesive composition is also described which comprises an acrylic monomeric material adapted for activation by a metal salt activator such as a copper salt, wherein the composition includes a calixarene derivative of formula I. In the gap-filling adhesive composition the calixarene derivative may be used jointly with a halogenated alkyl acrylate or methacrylate which is halogenated on the alkyl portion.

7 Claims, No Drawings

POLYMERIZATION CATALYSTS AND POLYMERIZATION PROCESS USING SUCH CATALYSTS

This application is a continuation-in-part of U.S. Ser. No. 088,945, filed Aug. 24, 1987, now U.S. Pat. No. 4,866,198, which is a continuation-in-part of U.S. Ser. No. 870,677, filed June 4, 1986, now U.S. Pat. No. 4,699,966, which is a continuation-in-part of U.S. Ser. No. 717,251, filed Mar. 28, 1985, now U.S. Pat. No. 4,642,362, and which is a continuation-in-part of U.S. Ser. No. 825,012, filed Jan. 31, 1986, now U.S. Pat. No. 4,695,615, and which is a continuation-in-part of U.S. Ser. No. 914,491, filed Oct. 2, 1986, now U.S. Pat. No. 4,718,966.

BACKGROUND OF THE INVENTION

1. Field of the Invention

This invention relates to a free radical polymerization process in which free radical sources or initiators normally soluble only in high polarity media (e.g. water) can be used in relatively low polarity media (e.g. acrylate resin systems). The invention also relates to polymerisation catalysts for use in such a process. In one aspect the invention concerns a process for polymerisation of an acrylic monomer adhesive composition using a metal salt applied to a surface as free radical initiator. It also relates to a process for achieving CTV (cure through volume) in an acrylic adhesive joint where a gap is left between two surfaces being joined.

2. Description of the Related Art

Free radical sources or initiators which are insoluble in organic media were previously only usable in water based polymerization systems such as in emulsion polymerizations. U.S. Pat. No. 4 326 049 Rasmussen has described a process for polymerizing olefinic monomeric material comprising adding a water-soluble free radical initiator/phase transfer agent complex to an organic liquid comprising free-radical polymerizable ethylenically unsaturated monomeric material and activating the same to produce free radicals. Several different classes of phase transfer agents are described, but the phase transfer agents specified in the claims are (i) a cation complex of an alkali or alkaline earth metal or ammonium cation and a neutral donor molecule selected from the group consisting of multidentate compounds, an amine selected from the group consisting of N,N'-dimethylpiperazine, 1,4-diazabicyclo octane, N,N,N',N'-tetramethylethylenediamine, piperazine hexamethyl phosphoric triamide amphoteric compounds; or (ii) a cation having the formula $(A_mM)+$ where A is an organic radical having from one to eighteen carbon atoms bonded to M by m covalent linkages and M is an element selected from Groups VA and VIA of the Periodic Table of Elements.

The preferred phase transfer agents are macrocyclic multidentate compounds referred to as "crowns", crown ethers, cryptates or cryptands, or "lantern" or "clam" compounds. The preferred "crowns" are the substituted and unsubstituted member of the 15-crown-5 and 18-crown-6 series, the most preferred being 18-crown-6. The free radical initiators used in the Examples of the Rasmussen Patent are limited to potassium and ammonium salts, more particularly potassium peroxydisulphate.

The present invention provides a free radical polymerisation process which comprises bringing together (a) monomeric material in a relatively low polarity medium, (b) a free radical source or initiator normally soluble only in high polarity media, and (c) a calixarene derivative of the formula

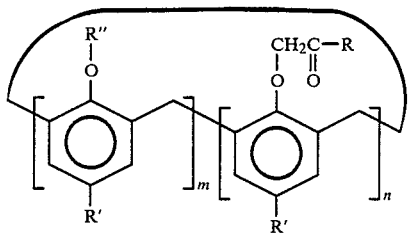

wherein m+n=4, 6 or 8 n=an integer greater than or equal to $\frac{1}{2}(m=n)$

R=hydrocarbyl, hydrocarbyloxy, substituted hydrocarbyl, substituted hydrocarbyloxy, aryl, hydrocarbylaryl, aryloxy, hydrocarbylaryloxy, substituted aryl, substituted hydrocarbylaryl, substituted aryloxy, or substituted hydrocarbylaryloxy;

R'=H, hydrocarbyl, aryl, hydrocarbylaryl, substituted hydrocarbyl, substituted aryl, or substituted hydrocarbylaryl;

R"=H, hydrocarbyl or substituted hydrocarbyl.

When m and n are greater than 1, the m aryl groups having the —OR" side chain may be interspersed around the ring between the aryl groups having the —OCH$_2$ C(O)R side chain.

In the above compounds, the hydrocarbyl groups shall preferably contain from 1 to 10 carbon atoms, more preferably from 1 to 5 carbon atoms and the aryl and hydrocarbylaryl groups shall preferably have from 6 to 20 carbon atoms, more preferably from 6 to 10 carbon atoms. Hydrocarbyl groups are preferred, especially alkyl or alkenyl groups. A substituted derivative of the foregoing may suitably be substituted with one or more halo groups or substituted or interrupted by one or more oxo groups. Halogen may be chlorine, bromine, fluorine or iodine.

In comparative experiments the present Applicants have found the selected calixarene derivatives to be more efficacious than the appropriate "crown" compound in inducing polymerisation and it was also found possible to employ free radical sources or initiators containing transition metals or lanthanides such as ceric ion salts.

In one aspect the present invention provides a free radical polymerisation catalyst comprising a combination of a water-soluble, organic-insoluble initiator and a calixarene derivative of formula I as defined above. In another aspect the invention provides a process for the free radical polymerisation of ethylenically unsaturated monomeric material which comprises bringing together (a) an organic medium containing the ethylenically unsaturated monomeric material, (b) a water soluble, organic-insoluble initiator, (c) a calixarene derivative of formula I as defined above.

In a further aspect, the invention provides a gap-filling adhesive composition comprising an acrylic monomeric material adapted for activation by a metal salt activator, wherein the composition includes a calixarene derivative of formula I.

In yet another aspect the invention provides a gap-filling adhesive composition as defined above wherein the calixarene derivative is used jointly with a halogenated alkyl acrylate or methacrylate which is halogenated on the alkyl portion.

It is believed that the halogenated organic compound assists in solubilising the metal salt in the acrylic monomer composition and facilitates its diffusion through the volume of the adhesive.

The term "acrylic monomer" as used in this Specification includes methacrylic monomers and mixed monomeric materials containing one or more acrylic monomers. The term "initiator" as used in this specification covers not only free radical sources which themselves initiate polymerisation but also compounds which activate the breakdown to free radicals of a free radical source. In the latter case, the free radical source may be soluble in the organic medium with the monomeric material while the activator is normally of low solubility in the organic medium but is solubilised therein because of the presence of the calixarene derivative. However the invention is applicable more widely to free radical sources which are not necessarily polymerisation initiators, and to the transport of free radical sources from a polar phase to a non-polar phase, the polar phase not necessarily being water. For example the low polarity medium may be hexane or petroleum ether while the high polarity phase may be propylene carbonate or dimethylsulfoxide.

Calixarene compounds are known and may be readily synthesised by methods described in C. Gutsche, Acc. Chem. Res., 16, 161-170 (1983) and references cited therein, the appropriate disclosures of which are incorporated herein by reference. Particular methods of synthesis for the calixarene derivatives exemplified herein are described in U.S. Pat. No. 4 556 700 Harris et. al. assigned to Loctite Limited and European Patent Application No. 0 259 016 of Loctite (Ireland) Limited. The most preferred compounds may be represented by formula I wherein R is ethoxy, methoxy, methyl or phenyl, R' is H or t-butyl, R" (if present) is alkyl, alkenyl or substituted alkyl or alkenyl, more particularly methyl, allyl or allyl acetate, and n is 4 or 6. Preparation of calixarene derivatives wherein at least some of the aryl groups have —O—R" substituents is described in European Patent Application No. 0196895 A2 of Loctite (Ireland) Ltd, particularly in Examples 2 and 3 thereof.

The ethylenically unsaturated monomeric material may be any of the monomers described in U.S. Pat. No. 4 326 049 Rasmussen, the disclosure of which is incorporated by reference. Particularly preferred are acrylic monomers which are well known in the art. It may suitably be an acrylate or methacrylate ester of a monohydric, dihydric, trihydric or polyhydric alcohol. It may include as a modifier or auxiliary polymerisable agent an epoxy or urethane system, or a prepolymer of a low molecular weight urethane or polyester capped with acrylate groups. It may also be an oligomer of an acrylate monomer.

Organic solvents which are known in the art for free radical polymerization may be used as the organic medium. Suitable examples are listed in U.S. Pat. No. 4 326 049 Rasmussen. Free-radical initiators known in the art may be used as the free radical source. Examples are listed in U.S. Pat. No. 4 326 049 Rasmussen. In addition in accordance with the present invention free-radical sources especially peroxide or hydroperoxide are used in conjunction with activator such as transition metal salt solutions as for example Loctite's Primer N product or copper or cobalt salt solutions described in U.S. Pat. No. 3672942 Loctite, and U.S. Pat. No. 4054480 National Starch and Chemical Corporation.

Activation of the free radical initiators may be achieved by conventional means e.g. by thermal, photochemical or chemical (redox) means.

DESCRIPTION OF THE PREFERRED EMBODIMENTS

The invention is illustrated in the following non-limiting Examples.

EXAMPLE 1

To a round-bottomed flask fitted with a magnetic stirrer and a nitrogen inlet, and immersed in an oil bath, was added 30 grams of n-butyl acetate and 10 grams of n-butyl acrylate. To this mixture was added 0.1 grams of sodium peroxydisulfate and a complexing agent of the type and in the amount specified in Table 1. The reaction flask was flushed with nitrogen and maintained under a nitrogen atmosphere at 80° for the time specified in Table 1. At the end of this time, the percentage conversion of monomer to polymer was determined gravimetrically. The results, recorded in Table 1, demonstrate the superior performance of a calixarene derivative in this system when compared to a more conventional complexing agent, 15-crown-5, which is used because it is preferential for sodium salts, whereas 18-crown-6, which was used by Rasmussen, is preferential for potassium salts.

TABLE 1

| Complexing Agent | Amount mmol | Reaction Time, hr. | % Conversion to Polymer |
| --- | --- | --- | --- |
| None | — | 24 | 0 |
| 15-Crown-5 | 0.16 | 22 | 33 |
| TBCA* | 0.05 | 24 | 41 |
| TBCA | 0.10 | 24 | 57 |
| TBCA | 0.20 | 24 | 63 |

TBCA = 5,11,17,23-tetra-t-butyl-25,26,27,28-tetra-(2-oxo-2 ethoxy)-ethoxy calix-[4]arene prepared as in Example 8 of U.S. Pat. No. 4 566 700 Harris et al.

EXAMPLE 2

The experiment outlined in Example 1 was repeated except that the calixarene derivative was HBCA*, the sodium peroxydisulfate was replaced by 0.1 grams of potassium peroxydisulfate, the butyl acetate solvent was replaced by ethyl acetate and the reaction temperature was 77° C. Results are listed in Table 2.

TABLE 2

| Complexing Agent | Amount mmol | Reaction Time, hr. | % Conversion to Polymer |
| --- | --- | --- | --- |
| None | — | 24 | 0 |
| HBCA* | 0.07 | 24 | 97.5 |

*HBCA = 5,11,17,23,29,35-hexa-t-butyl-37,38,39,40,41,42-hexa-(2-oxo-2-ethoxy)-ethoxy calix[6]arene prepared as in Example 1 of U.S. Pat. No. 4 566 700 but omitting the aluminium chloride treatment which would remove the t-butyl groups.

EXAMPLE 3

The experiment outlined in Example 1 was repeated except that the calixarene derivative was HECA*, that the sodium peroxydisulfate was replaced by 0.1 grams of ceric ammonium nitrate (CAN) or by 0.1 grams of ceric ammonium sulfate (CAS) and the reaction temperature was 85° C. Results are listed in Table 3.

TABLE 3

| Initiator | Complexing Agent | Amount mmol | Reaction Time, hr. | % Conversion to Polymer |
|---|---|---|---|---|
| CAN | None | — | 24 | 0 |
| CAN | HECA* | 0.09 | 24 | 20 |
| CAS | None | — | 22 | 25 |
| CAS | HECA* | 0.09 | 23 | 44 |

HECA* = 37,38,39,40,41,42-hexa-(2-oxo-2-ethoxy)-ethoxy calix[6]arene prepared as in Example 1 of U.S. Pat. No. 4 566 700.

EXAMPLE 4

The experiment described in Example 1 was repeated except that the n-butyl acrylate was replaced by N-vinyl pyrrolidone.

The results, listed in Table 4, show the rate accelerating effect of the calixarene when compared with a control reaction or a reaction involving a more conventional complexing agent.

TABLE 4

| Complexing Agent | Amount mmol | Reaction Time, min. | % Conversion to Polymer |
|---|---|---|---|
| None | — | 20 | 39 |
| None | — | 40 | 47 |
| TBCA | 0.09 | 20 | 92 |
| TBCA | 0.09 | 40 | 97 |
| 15-Crown-5 | 0.09 | 20 | 66 |
| 15-Crown-5 | 0.09 | 40 | 75 |

EXAMPLE 5

To an adhesive formulation based on 16.9% by weight hydroxypropyl methacrylate, 6.1% acrylic acid, 47.1% monomer B (a urethane acrylate prepared by reacting two moles of toluene diisocyanate with one mole of hydrogenated bisphenol A, diluting the reaction mixture with methyl methacrylate and further reacting it with two moles of hydroxyethyl methacrylate in the manner disclosed in Example V of U.S. Pat. No. 3,425,988), 23.6% monomer A (a urethane-acrylate reaction product of toluene diisocyanate and the hydroxy polyoxypropylene derivative of trimethylol propane (commercially available under the trademark PLURACOL T P 2450) having unreacted isocyanate functionality capped with hydroxyethyl methacrylate), 1% saccharin, 1% acetylphenylhydrazine hydrazine and 1.9% cumene hydroperoxide was added varying quantities of 5,11,17,23-tetra-tert-butyl-25,26,27,28-tetra(2-oxo-2-ethoxy) ethoxy calix[4]arene as described in Example 8 of U.S. Pat. No. 4 556 700.

The adhesive composition was stirred until all of the calixarene derivative had gone into solution, then tested on grit blasted mild steel lapshears primed one or both sides with brushed-on copper salt activator consisting of "Activator N" which is commercially available from Loctite (Ireland) Limited, Dublin.

The lapshears were at the gaps indicated in the tables below. The composition was cured for 24 hours at room temperature. The results of the tests shown in the Tables below demonstrate gap-filling or CTV (cure through volume) performance was improved markedly.

Also tested in conjunction with the calixarene derivative was 2,2,3,3 tetrafluoropropyl methacrylate (Rohm) which in theory was capable of improving solubility of the copper salt in the bulk of the adhesive. At a 5% level it did provide an improvement in CTV. However, when used in conjunction with the calixarene derivative the improvement was better than for either additive used separately (see below) i.e. we observed what appeared to be a synergistic effect.

| Grit Blasted Mild Steel Lapshears; 24 Hour Test; Room Temperature; 0.4 mm Gap; Single Sided Activation with copper salt | | |
|---|---|---|
| Additive with Adhesive | 82° C. Stability | Strength Tensile Shear daNcm-2 |
| 0 | ≧2 hr 40 min | 17 |
| 1% Calixarene derivative | ≧2 hr 40 min | 31 |
| 5% Tetrafluoropropyl-methacrylate | ≧2 hr 40 min | 26 |
| 1% Calixarene derivative + 5% Tetrafluoropropyl Methacrylate | ≧2 hr 40 min | 41 |

| 24 Hour Test; Room Temperature; Double Sided Activation with copper salt | | | |
|---|---|---|---|
| Additive with Adhesive | 82° C. Stability | Tensile Shear Zero Gap | daNcm$^{-2}$ 0.7 mm Gap |
| Zero | 2 hrs 30 mins | 207 | 12 |
| 0.3% Calixarene derivative | >2 hrs 8 mins | 199 | 13 |
| 1% Calixarene derivative | >2 hrs 8 mins | 227 | 29 |
| 5% Calixarene derivative | 2 hrs 8 mins | 203 | 46 |
| 5% Calixarene derivative + 5% Tetrafluoropropyl methacrylate | 1 hr 45 mins | — | 80 |

EXAMPLE 6

Preparation

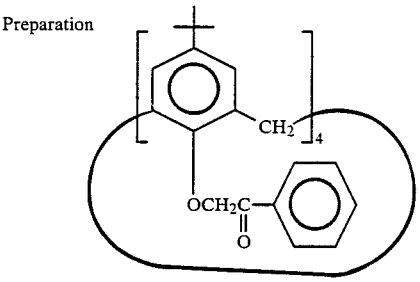

To 8.1 g (0.0125 mole) p-t-butylcalix-4-arene was added 7.5 g (0.05 mole) sodium iodide, 10.4 g (0.075 mole) anhydrous potassium carbonate, 7.7 g (0.05 mole) phenacyl chloride and 150 mls analar acetone. The entire was refluxed with stirring under nitrogen for 48 hours. After cooling to room temperature the reaction mixture was poured into 1 liter water to give a pale brown precipitate which was filtered off, taken up into dichloromethane and this organic solution washed with 5% aqueous sodium thiosulphate, followed by 5% aqueous sodium metabisulphite, water, 3% aqueous sulphuric acid, water; then dried with dried magnesium sulphate. Removal of volatiles, the last traces under vacuum, gave 14.1 g of crude product (buff coloured solid) which was boiled with 2 liters methanol; 9.2 g of buff coloured solid was filtered off and found to be 81% pure product. Recystallisation of the 9.2 g from 2-propanol gave 6.0 g of 99.5% product (43% overall yield) as colourless shiny needles which was characterised by i.r. spectroscopy, HPLC analysis and elemental anaylsis as title compound: mp 222°–228° C.

i.r. spectroscopy results: $\nu 1704$ (S) cm$^{-1}$ C=O

HPLC analysis results: Employing Waters Associates model 440 and micro Bondpak C18 reverse phase column; u.v. detector Pye Unicam PV 4020 set at $\lambda$m 280 nm; 1.5 mls/minute (20% water, 80% THF) isotactic; one main product 99.5% at 6.00 minutes.

Elemental Analysis results: (calculated for $C_{76}H_{80}O_8$: C: 81.39, H: 7.19; Found C: 81.68, H: 7.33).

EXAMPLE 7

An adhesive formulation similar to that of Example 5 but from a different batch was used to test the aryl calixarene derivative of Example 6. For comparative purposes, the same calixarene derivative as in Example 5 was also tested in this new batch of adhesive. The procedure was the same as in Example 5, the derivative of Example 5 being at a 3% level while the derivative of Example 6 was used at a 2% level. The results are set out below.

| | 24 Hour Test; Room Temperature; Double sided Activation with copper salt | | |
|---|---|---|---|
| Additive with Adhesive | 82° Stability | Tensile Shear Zero Gap | daNcm$^{-2}$ 0.7 mm Gap |
| Zero | >2 hrs 56 mins <4 hrs 00 mins | 138 | 4 |
| 3% Example 5 Derivative | >2 hrs 56 mins <4 hrs 00 mins | 193 | 12 |
| 2% Example 6 Derivative | >2 hrs 56 mins <4 hrs 00 mins | 228 | 11 |

I claim:

1. A free radical polymerisation process which comprises bringing together
   (a) an ethylenically unsaturated monomeric material in a relatively low polarity organic medium,
   (b) a water soluble, free radical source or initiator, and
   (c) a calixarene derivative of the formula I:

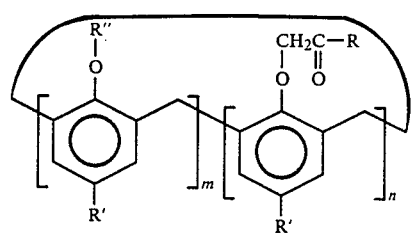

wherein m+n=4, 6 or 8 n=an integer greater than or equal to $\frac{1}{2}$ (m+n)

R=hydrocarbyl, hydrocarbyloxy, substituted hydrocarbyl, substituted hydrocarbyloxy, aryl, hydrocarbylaryl, aryloxy, hydrocarbylaryloxy, substituted aryl, substituted hydrocarbylaryl, substituted aryloxy, or substituted hydrocarbylaryloxy;

R'=H, hydrocarbyl, aryl, hydrocarbylaryl, substituted hydrocarbyl, substituted aryl, or substituted hydrocarbylaryl;

R''=H, hydrocarbyl or substituted hydrocarbyl.

2. A process according to claim 1 using a calixarene derivative wherein R'' is alkyl, alkenyl or substituted alkyl or alkenyl.

3. A process according to claim 1 using a calixarene derivative wherein R is ethoxy, methoxy, methyl or phenyl, R' is H or t-butyl, R'' (if present) is methyl, allyl or allyl acetate and n is 4 or 6.

4. A process according to claim 1 wherein (b) is a water soluble, organic-insoluble initiator.

5. A process according to claim 4 wherein the monomeric material is an acrylic monomer and the initiator is a metal salt.

6. A process according to claim 5 wherein the organic medium also contains a free radical source and the organic insoluble initiator is a copper salt which activates the breakdown to free radicals of the free radical source.

7. A free radical polymerisation catalyst comprising a combination of a water-soluble, organic-insoluble initiator and a calixarene derivative of formula I as defined in claim 1.

* * * * *